United States Patent [19]

Chang et al.

[11] Patent Number: 4,748,129

[45] Date of Patent: May 31, 1988

[54] ASSAY METHOD EMPLOYING FLUORESCENT CELL INCORPORATIVE DYE

[75] Inventors: Chiu C. Chang, Sunnyvale; Vartan Ghazarossian, Palo Alto; Edwin F. Ullman, Atherton, all of Calif.

[73] Assignee: Snytex (U.S.A.) Inc., Palo Alto, Calif.

[21] Appl. No.: 645,458

[22] Filed: Aug. 28, 1984

[51] Int. Cl.$^4$ ................. G01N 33/554; G01N 33/555
[52] U.S. Cl. ................... 436/519; 436/520; 436/536; 436/537; 436/800; 436/805; 436/807; 436/829; 424/3; 424/11
[58] Field of Search ............ 424/3, 11; 436/519, 436/520, 536, 537, 800, 805, 807, 829

[56] References Cited

U.S. PATENT DOCUMENTS

| | | | |
|---|---|---|---|
| 4,080,264 | 3/1978 | Cohen et al. | 436/520 |
| 4,319,882 | 3/1982 | Sharma | 424/11 |
| 4,424,201 | 1/1984 | Valinsky et al. | 436/800 |
| 4,436,825 | 3/1984 | Lalezari | 424/11 |
| 4,550,017 | 10/1985 | Liu et al. | 436/533 |
| 4,564,598 | 1/1986 | Briggs | 436/501 |
| 4,584,277 | 4/1986 | Ullman | 424/11 |

FOREIGN PATENT DOCUMENTS

| | | | |
|---|---|---|---|
| A20106685 | 10/1983 | European Pat. Off. | |
| 2041517 | 9/1980 | United Kingdom | 436/829 |

OTHER PUBLICATIONS

Smith, D. S., FEBS Letters, vol. 77, No. 1, (1977), pp. 25-27.
Briggs, et al., Science, vol. 212, (1981), pp. 1266-1267.
Briggs, et al., Proc. Natl. Acad. Sci. U.S.A., vol. 77, No. 8 (1980), pp. 4904-4908.
Kinsland, et al.; J. Biochem. Biophys. Meth., vol. 9, (1984), pp. 81-83.
Sprenger, et al., Angew. Chem. Internat. Edit, vol. 7, 530-535 (1968), Angew. Chem. 80, 541 (1968) German version.
Sprenger, et al., Angew. Chem. Internat. Edit. vol. 5, 894 (1966), Angew. Chem., 78, 938 (1966) German version.
Maahs et al., Angew. Chem. Internat. Edit., vol. 5, 888-893 (1966), Angew. Chem. 78, 927 (1966) German version.
Sprenger, et al., Angew. Chem. Internat. Edit., vol. 6, 553-554 (1967), Angew. Chem., 79, 581 (1967).
Angewandte Chemie International Edition, vol. 6, No. 1, Jan. 1967, Weinheim, pp. 553-554.
Angewandte Chemie International Edition, vol. 5, No. 1, Jan. 1966, Weinheim, pp. 894-895.

*Primary Examiner*—Sidney Marantz
*Assistant Examiner*—Stephen C. Wieder
*Attorney, Agent, or Firm*—Theodore J. Leitereg

[57] ABSTRACT

A method is provided for determining the presence in a sample of a member of a specific binding pair ("sbp member") consisting of ligand and its homologous receptor. The sample is combined in an aqueous medium with (1) a complementary sbp member wherein at least the sbp member or the complementary sbp member is bound to the surface of a cell and (2) a fuorescent agent capable of being incorporated into the cell. The presence of the sbp member is indicated by a change in fluorescence of the unseparated cell suspension as a result of agglutination of the cells.

The present invention has particular application to blood typing, for example, for the determination of the presence of blood group antigens A, B, AB, O, and D (Rh$_o$) and antibodies to such antigens.

34 Claims, No Drawings

ASSAY METHOD EMPLOYING FLUORESCENT CELL INCORPORATIVE DYE

BACKGROUND OF THE INVENTION

1. Field of the Invention

There is a continuing need for improved assay methods for the detection of an analyte in a sample. The analyte generally is a member of a specific binding pair consisting of ligand and its homologous receptor. Exemplary of sbp members are antigens and antibodies.

The mammalian red blood cells carry numerous antigens some of which must be accurately identified in both patient and donor for medical procedures such as transfusions. Accurate determination of blood groups, A, B, AB, O and D ($Rh_o$) is critically important. Also antibodies present in the blood to such antigens can be of diagnostic interest.

Conventionally, agglutination techniques are used on a microscope slide or in a tube. Improved rapid accurate screening of blood is desirable in view of the large numbers of samples which must be tested.

2. Description of the Prior Art

Identification of red blood cell antigens by agglutination techniques is standard, e.g., C. Hudson and F. C. Hay, *Practical Immunology,* Second Edition, Blackwell Scientific Publications, Oxford (1980), p. 139. U.S. Pat. No. 3,862,303 is exemplary of immunologial detection and identification of serological factors using carrier particles such as latex beads. Smith, FEBS Letters 77,25 (1977) describes a fluorescent immunoassay.

U.S. patent application Ser. No. 434,761, filed Oct. 15, 1982, now U.S. Pat. No. 4,550,017 concerns Fluorescence Screening for Blood Typing.

The use of laser beams and slits to differentiate particles based on their relative size by the correlation of fluorescence fluctuations in a relatively large sample volume is described by Briggs et al, *Science,* 212: 1266–1267, 1981, and by Nicoli et al., *Proc. Natl. Acad. Sci., USA,* 77: 4904–4908, 1980.

Various squarate dyes are discussed by Sprenger, et al., *Angew. Chem.,* 80, 541 (1968) [*Angew. Chem. Internatl. Edit,* Vol. 7: 530–535, 1968]; Sprenger, et al., *Angew. Chem.,* 79; 581, 1967 [*Angew. Chem. Internatl. Edit,* Vol. 6: 553–554, 1967]; Sprenger, et al., *Angew. Chem. internat. Edit,* 5: 894, 1966; and Maahs, et al., ibid., 5: 888, 1966.

The employment of a merocyanine dye for the detection of malignant leukocyte cells is described in U.S. Pat. No. 4,424,201.

U.S. Pat. No. 3,853,987 discloses an immunological reagent and radioimmunoassay. In a preferred method for detecting clumping of his reagents, the patentee dilutes a suspension of the reaction mixture and passes it through a flow cell in a spectrophotofluorometer.

SUMMARY OF THE INVENTION

A method is provided for determining the presence in a sample of a member of a specific binding pair ("spb member") consisting of ligand and its homologous receptor. The sample is combined in an aqueous medium with (1) a complementary sbp member wherein at least the spb member or the complementary sbp member is bound to the surface of a cell and (2) a fluorescent agent capable of being incorporated into the cell. The presence of the sbp member is indicated by a change in fluorescence of the unseparated cell suspension as a result of agglutination of the cells.

The present invention has particular application to blood typing, for example, for the determination of the presence of blood group antigens A, B, AB, O, and D ($Rh_o$) and antibodies to such antigens, as well as antibodies to antigens M, N, S, s, Lewis, Lutheran, Kell, Duffy, Kidd, etc.

DESCRIPTION OF THE SPECIFIC EMBODIMENTS

The subject invention provides a novel method for determining the presence of an analyte, usually a sbp member, in a sample without a separation step. The method employs a complementary sbp member where at least one of either the sbp member or the complementary sbp member is bound to the surface of a cell. Also employed in the method is a fluorescent cell incorporative agent. Preferably, when the sbp member in the sample is not bound to the surface of a cell, the fluorescent agent is combined with the sample by first incorporating the agnet into cells bound to a complementary sbp member and then combining the combination with the sample. When the sbp member on the sample is bound to the surface of a cell, the fluorescent agent is generally added to the sample prior to combining the sample with the complementary sbp member. Thus, the term "combining with the sample" is meant to include combining together two or more of the reagents mentioned above prior to combining the remaining reagents. The term "reagents" includes the sample, the complementary sbp member, and the fluorescent cell incorporative agent, and may further include any additional agents required for the successful operation of the subject method.

In carrying out one embodiment of the present method, the sample, the complementary sbp member, and the fluorescent cell incorporative agent are combined in an aqueous assay medium and a change in fluorescence of the mixture as a result of agglutination of the cells is then determined. The presence of the sbp member in the sample is indicated by this change in fluorescence.

The present method is adaptable to a wide variety of assay determinations for a wide variety of sbp member analytes. It is of special interest where at least one of the sbp member and complementary sbp member are a normal component of the cell surface. Cell surface sbp members include naturally occurring membrane components such as antigens, cell wall antigens, particularly bacterial cell walls, cell surface receptors including receptors for activating, growth, and inhibition factors, antibodies, HLA antigens, Fc receptors, hormone receptors, ion channels, glycolipids, lipoproteins, complement components, viral antigens, membrane bound enzymes, peptidoglycan, fungal antigens, idiotypic antigens and the like. Cell types of interest include leukocytes, bacteria, fungal cells, erythrocytes, reticulocytes, lymphocytes including monocytes, macrophage, B cells, T cells, eosinophils, etc. A particular adaptation of the present method is in the area of blood typing. Blood group antigens, as well as antibodies thereto, may be ascertained using the method described above.

The subject invention provides a novel method and is particularly useful for typing red blood cells or identifying red blood cell antigens and the antibodies thereto by using the red blood cells as a carrier of incorporated fluorescence where the cells agglutinate during the assay method. A change in fluorescence as a result the agglutination is determined and is an indication of the presence of a particular red blood cell antigen or antibody thereto. Substances which bind to red blood cell antigens, normally antibodies or lectins, are required to cause agglutination of the cells. In one embodiment of the present invention for determining blood group antigens, whole blood is combined with a fluorescent cell incorporative agent and a receptor for the antigen of interest in an aqueous medium, e.g., an appropriate buffer. If the antigen of interest is present on the surface of the red blood cells in the blood agglutination will occur and a change in fluorescence will be observed as an indication of the presence of the antigen of interest.

The receptor which is employed binds preferentially to the blood group surface antigens of interest. Thus, there will be a fluorometrically measurable change when a given antigen is present as compared to when that antigen is absent in a given red blood cell sample. For example, in the A, B, O system, if anti-A antibody were used, agglutination would occur and there would be a change in fluorescence if the analyte contained the A antigen of type A or type AB blood over that where the analyte contained blood types B or O.

In addition to antibodies, certain lectins are known to bind in varying degrees to red blood cell surface antigens, and are convenient receptors for use in the present assays.

The subject method can also be used for determining the presence of antibodies to a red blood cell antigen. In this approach, red blood cells having the surface antigen homologous to the antibody in question are employed in the assay. The antigen bearing cells and a fluorescent agent are preferably combined first and then combined with the sample in an aqueous medium. If the antibody in question is present in the sample, a change in fluorescence will occur as the result of agglutination. In this situation, a change in fluorescence would indicate the presence of the antibodies in question.

The present method is also important in cross-match determinations. In such a determination, blood from a donor and blood from a potential recipient are mixed and the mixture is treated in accordance with the method of the invention. Preferably, the cells from the donor will be combined with the fluorescent agent prior to combining with the patient's sample. Generally, a positive signal indicates that the match is incompatible.

The present method is simple and can be performed in a reasonably short period of time. For the most part, the reagents can be added simultaneously. Background interferences from free fluorescent agent and from endogenous materials in a sample are minimal. The change in fluorescence may be determined over a continuous background. A particular advantage of the present method is that no separation or washing step is necessary. The assay medium or mixture may be observed directly for a change in fluorescence as a result of agglutination of the cells.

Before proceeding further a number of terms will be defined. "Analyte"—the compound or composition to be measured, which is a sbp member and may be a ligand, which is mono- or polyvalent, that is, having one or a plurality of determinant sites, haptenic and antigenic, a single compound or plurality of compounds which share at least one common epitopic or determinant site; or a receptor.

"Sbp member"—a member of a specific binding pair, consisting of two different molecules, where one of the molecules has an area on the surface or in a cavity which specifically binds to a particular spatial and polar organization of the other molecule. The two members of a specific binding pair are referred to as ligand and receptor (antiligand) and are also referred to as homologous.

"Ligand"—any organic compound for which a receptor naturally exists or can be prepared;

"Receptor" (antiligand)—any macromolecular compound or composition capable of recognizing (having an enhanced binding affinity to) a particular spatial and polar organization of a molecule, i.e., epitopic or determinant site. Illustrative receptors include naturally occurring receptors, e.g., thyroxine binding globulin, antibodies, enzymes, Fab fragments, lectins, and the like. The term antibody is employed in this case as illustrative of, and to more generally denote, receptor.

"Complementary sbp member"—the homologous member of a specific binding pair where the sbp member is an analyte.

"Cell"—any one of the minute protoplasmic masses which make up organized tissue, comprising a mass of protoplasm surrounded by a membrane including nucleated and unnucleated cells and organelles.

"Fluorescent cell incorporative agent"—a compound of molecular weight less than 2000 capable of being incorporated into a cell and thereby causing the cell to be fluorescent, for example, a cell membrane soluble dye, a DNA intercalating dye, a vital dye or the like.

The fluorescent cell incorporative agent is preferably more fluorescent after incorporation into a cell. It may be capable of incorporation into the cell by virtue of being soluble in the cell membrane or of being transportable across the cell membrane and undergoing a chemical reaction that inhibits transport out of the cell. Fluorescent agents with high protein or carbohydrate affinity may also be useful in the present invention. Where the cells possess deoxyribonucleic acid (DNA), one may also employ fluorescent agents having an affinity for DNA. The fluorescent cell incorporative agent may be a hydrophobic dye that is subsequently rendered water soluble by chelation with a water compatible chelator.

The fluorescent cell incorporative agent should preferably have an absorption maximum greater than 450 nm, more preferably greater than 540 nm, to provide maximum avoidance of biological interference. For the most part, the absorption wavelength maximum should be 320 to 1000 nm, preferably 600 to 800 nm.

The molar extinction coefficient for the fluorescent cell incorporative agent at the wavelength of the exciting light should be as high as practical and should be greater than 1,000, preferably greater than 10,000, per mole per centimeter. Fluorescent cell incorporative agents are chosen to have a high quantum yield, normally greater than 0.05, preferably greater than 0.3 when incorporated in cells. The choice of the excitation wavelength depends on minimizing background fluorescence from the sample, maximizing fluorescence of the stained cells, and maximizing the intensity and reliability of the light source and filters. Particularly advantageous wavelengths are 488 nm, 515 nm and 633 nm because of the availability of these wave lengths from Argon, Argon, and Helium/Neon (He/Ne) lasers, respectively. In general, longer wavelengths minimize background. A He/Ne laser is particularly desirable and dyes with a high quantum yield and a high molar coefficient of extinction at 633 nm are therefore preferred.

In addition, it is desirable that the fluorescent cell incorporative agent have a large Stokes shift, preferably greater than 15 nm, more preferably greater than 30 nm. That is, it is preferred that there be a substantial spread or difference in wavelengths for the such fluorescent agent between its absorption maximum and emission maximum.

The fluorescent agent should remain substantially incorporated in the cell during the time of the assay, particularly where cells containing such fluorescent agent are to be mixed with a sample containing other cells. Furthermore, it is preferable that the fluorescent cell incorporative agent exhibit much stronger fluorescence when incorporated into a cell than when in an aqueous environment. By much stronger fluorescence is meant that the product of the extinction coefficient and the quantum yield at a given excitation wavelength be much greater when the fluorescent agent is incorporated in the cell than when the fluorescent agent is not incorporated in the cell. Although an increase in fluorescence is not required, it is usually preferable that the fluorescence of the cell incorporated agent be at least three, preferably at least ten, times that of the unincorporated fluorescent agent.

A further characteristic of the fluorescent cell incorporative agent is that it not interfere with binding of the sbp members, e.g., binding of the antigen and antibody. The fluorescent cell incorporative agent should preferably also exhibit a high affinity for the cell.

The number of fluorescent cell incorporative agent molecules per cell should be sufficient to conduct a meaningful assay, generally being about $10^2$ to $10^7$ of such molecules per cell, preferably $10^3$ to $10^6$ of such molecules per cell.

As mentioned above, a preferred class of fluorescent cell incorporative agents comprises fluorescent dyes that are soluble in the cell membrane, which means that the dyes are hydrophobic and will usually be amphiphilic to provide for sufficient water solubility to permit the agent to be incorporated in the cells in a reasonable time. A preferred group of membrane soluble dyes includes certain squarate dyes that have an absorption maximum greater than 600 nm and an appropriate molar extinction coefficient and Stoke's shift.

Exemplary of such dyes by way of illustration and not limitation are those of the formula:

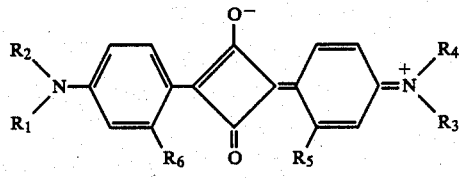

wherein $R_1$, $R_2$, $R_3$ and $R_4$, are each independently selected from the group consisting of alkyl of from 2 to 16, preferably lower alkyl of from 2 to 6, carbon atoms and aralkyl of from 2 to 16, preferably 2 to 6, carbon atoms wherein the groups may be the same or different and may be substituted with OH, CONHR$^1$, SR$^1$, OR$^1$ wherein R$^1$ is lower alkyl of from 1 to 6 carbon atoms, F, Cl, Br, I, NO$_2$, oxocarbonyl, CN, etc. and $R_5$ and $R_6$ are independently selected from the group consisting of hydrogen, methoxy, and hydroxyl. Some of these dyes are disclosed by Sprenger, et al., *Angew. Chem. internat. Edit.*, 5: 894, 1966.

Squarate dyes of the following formula are also exemplary of particular fluorescent cell incorporation agents in accordance with the present invention:

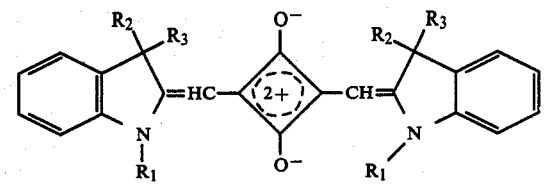

wherein $R_1$, $R_2$, and $R_3$ have been defined above. Some of these dyes are disclosed by Sprenger, et al. in *Angew. Chem. internat. Edit.*, 6: 553–554, 1967.

Other squarate dyes having the appropriate characteristics identified above for the fluorescent cell incorporative agent will be suggested to those skilled in the art.

The water solubility of the dyes can be enhanced by complexing the dye with a water solubility enhancing compound such as β-cyclodextrin and the like according to the teaching of, for example, Kinsland et al., *J. Biochem. Biophys. Methods* (1984) 9: 81–83.

Another class of fluorescent cell incorporative agents that may be used in the present invention are the "vital dyes". These dyes are derivatives of fluorescent dyes, which are membrane soluble and usually weakly fluorescent but are capable of becoming membrane insoluble and highly fluorescent after transport across the cell membrane. Once these derivatives are inside the cell, enzymes, for example, within the cell act upon the fluorescent dye derivative to prevent it from being transported out of the cell as readily as it was transported in. Exemplary of such dye derivatives are esters, such as acetates and the like, of fluorescent compounds such as the xanthene dyes, which include the fluoresceins derived from 3,6-dihydroxy-9-phenylxanthhydrol and rosamines and rhodamines, derived from 3,6-diamino-9-phenylxanthene. The rhodamines and fluoresceins have a 9-O-carboxyphenyl group, and are derivatives of 9-O-carboxyphenylxanthene. These compounds are commercially available with or without substituents on the phenyl group.

Other examples of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate. Other fluorescent compounds of interest include coumarins, e.g., umbelliferone.

Another class of fluorescent cell incorporative dyes that may be employed in the present invention are those possessing an affinity for DNA or RNA. As mentioned above, such dyes may be used in assays in which cells possessing DNA are involved. Exemplary of such dyes are DNA intercalating agents, which are generally well known compounds and are, for the most part, commercially available. Representative of such agents are acriflavine, acriflavine hydrochloride, and like acridine derivatives, and ethidium halides such as ethidium bromide.

Another class of fluorescent cell incorporative agents are those dyes or stains having a high affinity for proteins or carbohydrates. Such agents include, by way of example and not limitation, pyrene and naphthalene sulfonates, stilbene dimaleimides, salicylate maleimides, pyrene and coumarin isothiocyanates, dansyl compounds such as dansyl azide and so forth, anthracene carboxaldehyde carbohydrazones, common bacterial stains and the like. Examples of the above agents are found in the March 1981 catalog of Molecular Probes, Inc., Junction City, Oreg., and in Kodak Biological Stains and Related Products, publication number JJ-281-51.

The invention will next be described in detail using a blood sample as exemplary of the assay sample and blood group antigens, or antibodies thereto, as exemplary of sbp members that may be determined in accordance with the present method. This description is by way of illustration only and is not meant to limit the scope of the present invention.

In carrying out an assay for a blood group antigen in accordance with the present invention, a blood sample optionally in a buffered aqueous medium comprising greater than 5%, preferably greater than 20%, more preferably greater than 50%, blood by volume is employed. The pH of the buffered aqueous medium is usually about 5 to 9, preferably about 6 to 8. The sample is mixed with appropriate amounts of a fluorescent cell incorporative agent and a complementary sbp member, which amounts generally should be sufficient to result in a meaningful assay. The amount of the fluorescent cell incorporative agent depends upon the nature of the cells and the nature of the agent. Usually, about 0.1 to 100 μg, preferably about 1 to 10 μg, of fluorescent cell incorporative agent are employed per ml of blood. The amount of complementary sbp member employed is determined empirically and is usually between 0.01 and 1000 times the amount of sbp member, preferably 0.1 to 100 times the amount of sbp member.

Where the fluorescent cell incorporative agent has low water solubility, the blood sample may first be mixed with the fluorescent agent in a suitable organic polar solvent to facilitate incorporation of such agent into the cell. The organic solvent will generally have from 1 to 6 carbon atoms and from 1 to 3 heteroatoms selected from the group consisting of oxygen, nitrogen, and sulfur. Exemplary of such solvents are dimethylformamide, dimethylsulfoxide, hexamethylphosphoramide, and the like. Next, the mixture is combined with the complementary sbp member.

The sample, fluorescent cell incorporative agent, and complementary sbp member are combined and incubated under conditions that will provide for agglutination of the cells when the sbp member of interest is present. Incubation times may vary widely depending on the surface density of the sbp member, the concentration of the cells and the complementary sbp member and the reaction conditions including the addition of agglutination enhancers such as polybrene, dextran or dextran derivatives, low ionic strength medium, serum albumin, polyethyleneglycol, and the like. Desirable incubation times are about 10 to 600 sec, preferably about 10 to 200 sec, at mild temperatures usually about 10° to 37° C.

In reverse blood typing for the determination in a whole blood sample of antibodies to a particular blood group antigen, the sample is combined in an aqueous buffered medium with red blood cells of the particular type, A or B, of interest. The fluorescent cell incorporative agent is preferably incorporated into such cells prior to combining with the sample, in a manner and amounts similar to that for incorporation of such agent into the red blood sample as described above. The medium is then held for a period and at a temperature as mentioned above.

Following the above holding period, the medium is examined to determine any change in fluorescence as a result of agglutination of the cells.

To this end one may use a non-flow cytometric technique in which a small diameter beam of light produced by means of slits or preferably a laser is used to differentiate particles based on their relative size. This technique employs fluorescent pulse height analysis or correlation of fluorescence fluctuations: Briggs, et al., "Homogeneous Fluorescent Immunoassay," *Science*, 212, 1266–1267 (1981) and Nicoli, et al., "Fluorescence Immunoassay Based on Long Time Correlations of Number Fluctuations," *Proc. Natl. Acad. Asci. USA*, 77(8), 4904–4908 (1980).

A preferred method for determining a change of fluorescence in accordance with the present invention involves the use of the fiber optic cytometer described in U.S. patent application Ser. No. 397,285 filed July 12, 1982, the disclosure of which is incorporated herein in its entirety. In the application, method and apparatus are provided for determining the presence of particles in a dispersion in relation to the detection of the presence or amount of the material of interest. An optical fiber is used to define a relatively small volume from which fluorescent light can be received and counted. The volume is related to the volume in which there is likely to be only a single particle which results in a predetermined fluctuation. By employing a variety of techniques, which allow for changes in fluorescence fluctuations in relation to the presence of an analyte in a sample, the amount of analyte present may be determined. The fluctuations are observed over a period of time in a static mode or by sampling a plurality of volumes in the sample. By comparing the observed results with results obtained with assay solutions having a known amount of analyte, the amount of analyte can be quantitatively determined.

As a control, a known amount of blood group antigen or antibody in question is incorporated into an appropriate medium and treated as described above for the sample containing the unknown analyte. The change in fluorescence for the control is compared with the change in fluorescence for the unknown sample as an indicator of the presence of the blood group antigen or antibody thereto in question.

EXAMPLES

The invention is further demonstrated by the following illustrative examples.

EXAMPLE 1

Preparation of 2-(p-Diethylamino-m-hydroxyphenyl)-4-(4-diethylimmonio-2-hydroxy-2,5-cyclohexadienylidene)-3-oxo-1-cyclobutenolate (DEAS)

DEAS was prepared as follows: Squaric acid (741 mg, 65 mmole) was mixed with stirring, with 2.16 g, 13 mmole 3-N,N-diethylamino-phenol in 90 ml of n-butanol:toluene (2:1). The mixture was refluxed overnight with azeotropic removal of water. Progress of the reaction was followed by thin layer chromatography (tlc) using methanol:toluene (1:9). Next, the reaction mixture was distilled to remove about 40 ml of toluene, and then the reaction mixture was cooled to room temperature. Crystalline product was separated by filtration and dried at room temperature to give 2.5 g of product. UV (DMF) λ max 650 nm, ε=240,000, fluorescence (DMF) 650/666 nm.

EXAMPLE 2

Assay for the Determination of the D (Rho) Blood Group Antigen

A saturated solution of DEAS in dimethylformamide (DMF) was prepared and then diluted 1:10 (by volume) with DMF. Fifty μl of the diluted DEAS solution was mixed dropwise with 1 ml of an O (Rho) positive whole blood sample under continuous vortexing. Ten μl of this mixture was mixed with 10 μl of antibody (commercially available typing reagent) specific for the D ($Rh_o$) blood group antigen. The mixture was held for one minute at ambient temperature and then diluted with 1.5 ml of phosphate buffer containing serum albumin and sucrose.

The medium was analyzed for a change in fluorescence as a result of agglutination of cells by means of the limited volume method and apparatus for particle counting disclosed in U.S. Ser. No. 397,285, filed July 12, 1982, now U.S. Pat. No. 4,564,598.

The single fiber end of a "Y"-shaped fiber optics coupler obtained from Kaptron, Inc., Palo Alto, Calif. (Splitter-Monitor, Model FOMS-850-P), was submerged in the medium. The fiber had a diameter of 50 microns and produced an excitation cone with a half angle of 12° and an effective sampling volume of $1 \times 10^{-7}$ ml. Excitation light from a He-Ne laser (632.9 nm) was fed into one of the two branch fibers. The portion of the fluorescence emitted from the cells which entered the submerged fiber end was split at the fiber juncture to transmit equal halves back along the two branch fibers. The portion traveling through the second branch fiber was then read on a high-gain EMI photomultiplier after filtering out interference within gate times of one millisecond at the rate of one every 0.1 second for periods of time ranging from 50 to 500 seconds. The average number of fluorescent pulses per gate time was then determined by computer.

Two types of control runs were made to establish a standard emission level.

(a) Samples that were types as D ($Rh_o$) negative by conventional type were assayed in the same way.

(b) A commercially available "Rh control" reagent which includes all the ingredients of a D ($Rh_o$) typing reagent except for the antibody was used in the above assay in place of the antibody reagent.

The results from samples from five positive and five negative individuals are summarized in Table 1.

TABLE 1

| Type | Signal* |
| --- | --- |
| D ($Rh_o$) positive | 84 |
|  | 108 |
|  | 72 |
|  | 46 |
|  | 74 |
| D ($Rh_o$) negative | 18 |
|  | 23 |
|  | 22 |
|  | 17 |
|  | 20 |
| Control | 21 |
|  | 19 |

TABLE 1-continued

| Type | Signal* |
| --- | --- |
|  | 17 |

*Signal was obtained by fluctuation analysis as described in the specification, Signals greater than 40 were regarded as positive.

EXAMPLE 3

Assay for the Determination of the Antibody Specific for the A Blood Group Antigen Whole type A blood was centrifuged at 2800 rpm and the supernatant and buffy coat of the white cells were removed by aspiration. The packed cells were washed free of plasma using isotonic buffered saline and suspended at 50% hematocrit in buffer containing 10% bovine serum albumin.

A saturated solution of DEAS in DMF was prepared and diluted 1:10 (by volume) with DMF. Fifty μl of the diluted DEAS solution was mixed dropwise under continuous vortexing with 1 ml of the above type A cell suspension.

Ten μl of the above suspension was mixed with 20 μl of a whole blood sample. The mixture was held for one minute at ambient temperature diluted with 3 ml of buffer containing serum albumin and dextran, and analyzed as described above in Example 2 using the limited volume method and apparatus for particle counting. The results are summarized in Table 2.

TABLE 2

| Group* | Signal** |
| --- | --- |
| A | 18 |
|  | 23 |
|  | 25 |
|  | 13 |
|  | 18 |
| B | 112 |
|  | 110 |
|  | 91 |
|  | 107 |
|  | 56 |
| AB | 35 |
|  | 25 |
|  | 19 |
|  | 22 |
|  | 18 |
| O | 106 |
|  | 134 |
|  | 81 |
|  | 116 |
|  | 80 |
| Control*** | 15 |
|  | 18 |
|  | 16 |

*Samples from five separate individuals having the listed blood groups were tested.
**Signal was obtained by fluctuation analysis as described in specification, Signals greater than 40 were regarded as positive.
***Control signals were obtained by reacting the A cells with blood from individuals who were known to be of AB type.

EXAMPLE 4

The assay of Example 2 was repeated for blood group antigens A, B, and O using antibody specific for the A(αA) and B(αB) blood group antigens and antibodies obtained from type O individuals (αA,B), respectively. DEAS was complexed with β-cyclodextrin following the teaching of Kinsland, supra. The results are summarized in Table 3.

TABLE 3

| Blood Type | Reagent | Signal* |
|---|---|---|
| A | αA | 98 |
|   | αB | 13 |
|   | αA, B | 252 |
|   | Control - no reagent | 11 |
| B | αA | 10 |
|   | αB | 65 |
|   | αA, B | 272 |
|   | Control - no reagent | 16 |
| O | αA | 18 |
|   | αB | 20 |
|   | αA, B | 34 |
|   | Control - no reagent | 13 |

*Signal was obtained by fluctuation analysis as described in the specification. Signals greater than 40 were regarded as positive.

The above data demonstrate that the method of the invention has utility for assaying for a wide variety of analytes and has particular utility in blood typing. The method is simple and rapid. Generally, the method may be performed in a single step. The effects, on the sensitivity of the assay, of background interference from other components of a sample are minimized. The result of the assay may be obtained without a separation or washing step.

Although the foregoing invention has been described in some detail by way of illustration and example for purposes of clarity and understanding, it will be obvious that certain changes or modifications may be practiced within the scope of the appended claims.

What is claimed is:

1. A method for determining in a sample the presence of a member of a specific binding pair ("sbp member") consisting of ligand and its homologous receptor, which method comprises-
    (a) combining in an aqueous medium (1) a sample, (2) a complementary sbp member wherein at least one of said sbp member or said complementary sbp member is bound to the surface of a cell and (3) a fluorescent dye capable of being incorporated into said cell and
    (b) without separating said cells from said aqueous medium determining a change in fluorescence as a result of agglutination of said cells, said change being an indication of the presence of said sbp member.

2. The method of claim 1 wherein said sbp member is a cell surface member.

3. The method of claim 1 wherein said complementary sbp member is a receptor for a surface antigen.

4. The method of claim 1 wherein said cell is a red blood cell.

5. The method of claim 1 wherein said change in fluorescence is determined by a non-flow cytometry technique.

6. The method of claim 1 wherein said change in fluorescence is determined by a fiber optic cytometer.

7. The method of claim 1 wherein said fluorescent dye is a membrane soluble dye.

8. The method of claim 1 wherein said fluorescent dye is a squarate dye.

9. The method of claim 1 wherein said fluorescent dye exhibits a fluorescence when incorporated into said cell at least three times the fluorescence of the unincorporated fluorescent dye.

10. The method of claim 1 wherein said fluorescent dye is incorporated into said cells prior to combining with said aqueous medium.

11. A method for determining in a sample of whole blood the presence of a member of a specific binding pair ("sbp member"), which method comprises
    (a) combining in an aqueous medium (1) a sample, (2) a complementary sbp member wherein at least one of said sbp member or said complementary sbp member is bound to the surface of a cell and (3) a fluorescent dye capable of being incorporated into said cells and
    (b) without separating said cells from said aqueous medium, determining a change in fluorescence as an indication of the presence of said sbp member.

12. The method of claim 11 wherein said change in fluorescence is determined by a non-flow cytometric technique.

13. The method of claim 11 wherein said change in fluorescence is determined by a fiber optic cytometer.

14. The method of claim 11 wherein said fluorescent dye is a membrane soluble dye.

15. The method of claim 11 wherein said fluorescent dye exhibits a fluorescence when incorporated into said cells at least three times the fluorescence of the unincorporated fluorescent dye.

16. The method of claim 11 wherein said fluorescent dye is a squarate dye.

17. The method of claim 11 wherein said cells are red blood cells.

18. The method of claim 11 wherein said sbp member is a surface antigen.

19. The method of claim 18 wherein said surface antigen is selected from the antigens indicative of blood types selected from the group consisting of type A and type B.

20. The method of claim 18 wherein said surface antigen is the D blood group antigen.

21. The method of claim 18 wherein said surface antigen is an immunoglobulin.

22. The method of claim 11 wherein said change in fluorescence is a result of agglutination of said cells.

23. The method of claim 11 wherein said determination of Step b is compared to a sample having a known amount of a red blood cell antigen.

24. The method of claim 11 wherein said fluorescent dye has a molar extinction coefficient of greater than 10,000 $M^{-1} CM^{-1}$ at 633 nm.

25. The method of claim 11 wherein said fluorescent dye exhibits at least three times the fluorescence in a lipid environment relative to an aqueous environment.

26. The method of claim 11 wherein said fluorescent dye is incorporated into said cells prior to combining with said aqueous medium.

27. The method of claim 11 wherein said fluorescent dye is a squarate dye of the formula selected from the group consisting of

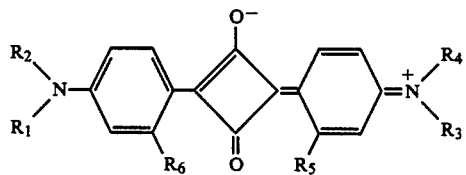

wherein $R_1$, $R_2$, $R_3$, and $R_4$ are independently selected from the group consisting of a alkyl of from 2 to 16 carbon atoms and aralkyl of from 2 to 16 carbon atoms and aralkyl of from 2 to 16 atoms wherein the groups may be the same or different and may be substituted with a substituent selected from the group consisting of OH, CONHR$^1$, SR$^1$, OR$^1$ wherein R$^1$ is lower alkyl of from 1 to 6 carbon atoms, F, Cl, Br, I, NO$_2$, oxocarbonyl and CN, R$_5$, and R$_6$ are independently selected from the group consisting of hydrogen, methoxy, and hydroxyl, or

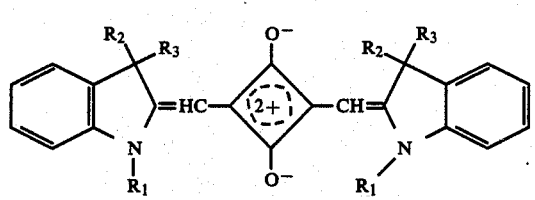

wherein R$_1$, R$_2$, and R$_3$ are independently selected from the group consisting of alkyl of from 2 to 16 carbon atoms and aralkyl of from 2 to 16 carbon atoms wherein the groups may be the same or different and may be substituted with a substituent selected from the group consisting of OH, CONHR$^1$, SR$^1$, OR$^1$ wherein R$^1$ is lower alkyl of from 1 to 6 carbon atoms, F, Cl, Br, I, NO$_2$, oxocarbonyl, and CN.

28. A method for determining in a sample of whole blood the presence of a member of a specific binding pair ("sbp member"), which method comprises
  (a) combining in an aqueous medium (1) a sample, (2) a complementary sbp member wherein at least one of said sbp member or said complementary sbp member is bound to the surface of a cell and (3) a fluorescent dye capable of being incorporated into said cells and
  (b) without separating said cells from said aqueous medium, determining a change in fluorescence by a non-flow cytometric technique as a result of agglutination of said cells, said change being an indication of the presence of said sbp member.

29. The method of claim 28 wherein said fluorescent dye is incorporated into said cells prior to combining with said aqueous medium.

30. The method of claim 28 wherein said fluorescent dye is a squarate dye.

31. In a method for typing red blood cells comprising treating red blood cells under conditions to achieve an agglutination of said cells and determining the extent of agglutination as an indication of the presence or absence of a particular red blood cell type, the improvement which comprises combining said cells with a fluorescent dye capable of being incorporated into said cells prior to said determining.

32. The method of claim 31 wherein said fluorescent dye is a squarate dye.

33. The method of claim 31 wherein said fluorescent dye has an absorption wavelength of greater than 600 nanometers.

34. The method of claim 31 wherein said fluorescent dye is a squarate dye of the formula selected from the group consisting of

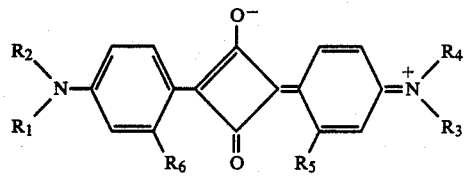

wherein R$_1$, R$_2$, R$_3$, and R$_4$ are independently selected from the group consisting of a alkyl of from 2 to 16 carbon atoms and aralkyl of from 2 to 16 carbon atoms and aralkyl of from 2 to 16 atoms wherein the groups may be the same or different and may be substituted with a substituent selected from the group consisting of OH, CONHR$^1$, SR$^1$, OR$^1$, wherein R$^1$ is lower alkyl, F, Cl, Br, I, NO$_2$, oxocarbonyl, and CN, R$_5$, and R$_6$ are independently selected from the group consisting of hydrogen, methoxy, and hydroxyl, or

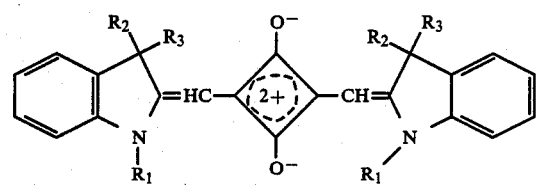

wherein R$_1$, R$_2$, and R$_3$ are independently selected from the group consisting of alkyl of from 2 to 16 carbon atoms and aralkyl of from 2 to 16 carbon atoms wherein the groups may be the same or different and may be substituted with a substituent selected from the group consisting of OH, CONHR$^1$, SR$^1$, OR$^1$, wherein R$^1$ is lower alkyl of from 1 to 6 carbon atoms, F, Cl, Br, I, NO$_2$, oxocarbonyl, and CN.

* * * * *